United States Patent [19]

Cafaro

[11] Patent Number: 5,447,650
[45] Date of Patent: Sep. 5, 1995

[54] COMPOSITION FOR PREVENTING THE ACCUMULATION OF INORGANIC DEPOSITS ON CONTACT LENSES

[75] Inventor: Daniel P. Cafaro, Santa Ana, Calif.

[73] Assignee: Allergan, Inc., Irvine, Calif.

[21] Appl. No.: 132,606

[22] Filed: Oct. 6, 1993

[51] Int. Cl.⁶ .......................... C11D 3/06; C11D 7/16
[52] U.S. Cl. ......................................... 252/135; 8/507;
252/174.12; 252/DIG. 12; 422/28; 424/78.04;
427/2.1; 427/164; 436/192; 436/264; 514/839;
514/840
[58] Field of Search ................. 427/2, 164, 430.1;
8/507; 422/28; 435/192, 264; 424/78.04;
514/839, 840; 252/174.12, 135, DIG. 12

[56] References Cited

U.S. PATENT DOCUMENTS

| | | | |
|---|---|---|---|
| 3,954,965 | 5/1976 | Boghosian et al. | 424/81 |
| 4,128,318 | 12/1978 | Sieglaff et al. | 351/160 R |
| 4,395,346 | 7/1983 | Kleist | 252/135 |
| 4,405,482 | 9/1983 | Hayes et al. | 252/99 |
| 4,521,375 | 6/1985 | Houlsby | 422/29 |
| 4,543,200 | 9/1985 | Sherman | 252/106 |
| 4,568,517 | 2/1986 | Kaspar et al. | 422/30 |
| 4,585,488 | 4/1986 | Giefer | 134/27 |
| 4,650,843 | 3/1987 | Yokoyama et al. | 351/160 H |
| 4,748,992 | 6/1988 | Giefer | 422/301 |
| 4,767,559 | 8/1988 | Kruse et al. | 252/106 |
| 4,826,658 | 5/1989 | Kay | 422/30 |
| 4,829,001 | 5/1989 | Mencke et al. | 435/264 |
| 4,863,627 | 9/1989 | Davies et al. | 252/95 |
| 4,899,914 | 2/1990 | Schweigl et al. | 222/394 |
| 5,011,661 | 4/1991 | Schäfer et al. | 422/30 |
| 5,145,644 | 8/1992 | Park et al. | 422/28 |
| 5,171,526 | 12/1992 | Wong et al. | 422/28 |

FOREIGN PATENT DOCUMENTS

| | | |
|---|---|---|
| 27227/84 | 10/1984 | Australia . |
| 426489 | 5/1991 | European Pat. Off. . |
| 436466 | 7/1991 | European Pat. Off. . |
| 514311 | 11/1992 | European Pat. Off. . |
| 05695 | 10/1986 | WIPO . |
| 12825 | 9/1991 | WIPO . |
| 9112826 | 9/1991 | WIPO . |
| 04922 | 4/1992 | WIPO . |
| 9401800 | 1/1994 | WIPO . |

*Primary Examiner*—Michael Lusignan
*Attorney, Agent, or Firm*—Jeffer, Mangels, Butler & Marmaro

[57] ABSTRACT

A composition including a neutralizing system and a sequestering agent is described which prevents the accumulation of inorganic deposits on contact lenses, particularly when used regularly in a conventional hydrogen peroxide disinfection regimen. The neutralizing system includes at least one reducing agent, a reductase, or both. The sequestering agent preferably is gluconic acid, a polymetaphosphate or their salts. Sodium hexametaphosphate is the most preferred sequestering agent; catalase is the most preferred agent for use as the neutralizing system.

7 Claims, No Drawings

COMPOSITION FOR PREVENTING THE ACCUMULATION OF INORGANIC DEPOSITS ON CONTACT LENSES

FIELD OF THE INVENTION

The invention relates to a method and composition for preventing the accumulation of inorganic deposits on contact lenses. It also relates to the removal of inorganic contaminants which have formed deposits on contact lenses.

BACKGROUND OF THE INVENTION

One of the inherent problems associated with the use of contact lenses for vision correction is the tendency for inorganic and organic contaminants to accumulate on the lenses over time. As these deposits form, they may not only interfere with the wearer's vision, but can also cause discomfort and eventually may damage the lens.

While protease-containing compositions will quickly remove proteinaceous deposits from contact lenses, many inorganic deposits are not as easily removed. For example, removal of the common calcium chloride and calcium phosphate deposits generally requires that heat be applied to the lenses as part of a regular cleaning regime.

One approach to removing inorganic deposits from heavily soiled lenses is described in U.S. Pat. No. 4,395,346 to Kleist. In the disclosed method, the lenses are submersed in an aqueous solution containing a sequestering agent consisting of a polymetaphosphate, gluconic acid, and/or their salts. This solution is mechanically heated to between 40° C. and 100° C. (preferably at least 80° C.), and is used to soak the lenses for extended periods (which can be shortened to 20 minutes or less where the lenses are also contacted with a protease).

While effective, this approach to removal of inorganic deposits has several drawbacks. Principal among these is the need to mechanically supply a sufficient level of heat to activate the sequestering agent and allow cleaning to occur in a reasonably short period of time. The need to use a mechanical heat source not only adds to the cost of contact lens use, it also requires the exercise of additional effort and skill to correctly clean the lenses. For example, if the lenses are exposed to too much heat they may be damaged.

A need, therefore, exists for a simple, self-activating system for limiting the accumulation of inorganic deposits on contact lenses. The present invention satisfies that need by providing compositions which assist in preventing deposits from accumulating on contact lenses without the use of externally supplied heat.

SUMMARY OF THE PREFERRED EMBODIMENTS

The present invention is directed to ophthalmically safe compositions for use in preventing the accumulation of inorganic deposits on contact lenses and methods for using the compositions. Each composition includes a sequestering agent and a neutralizing system which is capable of neutralizing hydrogen peroxide ($H_2O_2$) in an exothermic reaction. The sequestering agents are selected from the group consisting of gluconic acid, the polymetaphosphates, and their salts. The neutralizing system may include at least one reducing agent and/or a reductase, and preferably includes both.

In a preferred embodiment of the invention, the sequestering agent and the neutralizing system are in dry form and are combined in a tablet. Alternatively, the sequestering agent and neutralizing system can be combined in a capsule, aqueous solution or powder. The composition can also contain a buffer and biocides as well as fillers or other inert delivery agents known to those skilled in the art which will not affect the activity of the active ingredients.

If a reductase is present, it is one which is not catalytically reactive until exposed to hydrogen peroxide. The reductase does not, therefore, degrade or otherwise react with the sequestering agent. Preferably, the reductase is catalase.

The compositions of the invention are used in an aqueous solution of hydrogen peroxide. The hydrogen peroxide is preferably used to disinfect contact lenses in a conventional disinfection regimen. After the lenses are disinfected, the composition of the invention is added (either separately or by delayed-release) to the hydrogen peroxide solution. The neutralizing system in the composition reacts with the hydrogen peroxide, thereby releasing heat in sufficient quantity to activate the sequestering agent.

The degree to which any inorganic deposits on the lenses are removed depends on the condition of the lenses and the length of time that they are exposed to the sequestering agent. Generally, without external application of additional heat, the sequestering agents would not be expected to completely remove the inorganic deposits. The composition of the invention is therefore most effective in preventing the accumulation of inorganic deposits on contact lenses if used regularly as part of a disinfection regimen.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

The following definitions are provided to simplify discussion of the invention. They should not, therefore, be construed as limiting the invention, which is defined in scope solely by the appended claims.

"Preventing the accumulation" of inorganic deposits denotes that the amount of inorganic deposits on a contact lens is reduced, or at the least not increased, due to treatment of the lens according to a method of the present invention.

"Substantially deposit-free" refers to a contact lens on which inorganic deposits are not present or, if present, are not of sufficient quantity to interfere with the wearer's vision or to cause discomfort.

"Reducing agent" refers to a nonenzymatic compound which is capable of neutralizing hydrogen peroxide (i.e., reducing it to water and oxygen).

"Reductase" refers to an enzyme which is capable of neutralizing hydrogen peroxide.

"Neutralizing system" refers to a component in the composition of the invention which is capable of neutralizing hydrogen peroxide. The neutralizing system can contain one or more reducing agents, a reductase, or both.

"Reductase neutralizing system" refers to a neutralizing system which consists essentially of a reductase.

"Reduction neutralizing system" refers to a neutralizing system which consists essentially of one or more reducing agents.

"Catalytic reduction neutralizing system" refers to a neutralizing system which consists essentially of a reductase and one or more reducing agents.

The primary active ingredients of the composition of the invention are a sequestering agent and a neutralizing system, that is, one or more reducing agents which are capable of neutralizing hydrogen peroxide. The sequestering agent which can be used in the invention are typically calcium sequestering agents such as gluconic acid, the polymetaphosphates, and/or salts thereof. Suitable polymetaphosphates include sodium polymetaphosphates such as sodium trimetaphosphate, sodium tetrametaphosphate and sodium hexametaphosphate, with the latter being the most preferred compound for use in the invention. Salts of gluconic acid which can be used in the invention include common inorganic salts such as the sodium, potassium and calcium salts as well as other salts such as calcium borogluconate. All of these compounds are well known in the art and are commercially available.

Reducing agents which can be present in the neutralizing system of the invention are well-known in the art and include ascorbic acid, sodium ascorbate, pyruvate or thiosulfate. To control the reaction between the reducing agent and the hydrogen peroxide in the disinfecting solution to be used in with the inventive compositions, a reductase can also be included in the neutralizing system as a catalyst. Alternatively, the reductase can itself be used to neutralize the hydrogen peroxide without use of a reducing agent. In this alternative embodiment, less heat is produced from the reaction with hydrogen peroxide than would be produced in the presence of a reducing agent.

In any event, the reaction is sufficient to maintain the lenses in a substantially deposit-free state when the enzymatic neutralizing system/sequestering agent composition is applied regularly (and preferably throughout the useful life of the lenses).

In those embodiments of the invention which include a reductase, the preferred reductase is catalase ($H_2O_2$ oxidoreductase; EC1.11.1.6). Catalase is available commercially in both dry and aqueous forms. For purposes of economy, a reductase neutralizing system comprised of catalase is the preferred neutralizing system for use in the inventive composition.

Preferred formulations of the composition of the invention are as follows. The sequestering agent is preferably between about 0.01 and 20% of the total composition by weight, most preferably about 8 to 12% w/w, which represents a final concentration in solution (10 ml liquid volume) of about 0.1% w/v. If present, the quantity of reducing agent used will depend on whether a reductase is also present. If used alone, the quantity of reducing agent will correspond to the stoichiometric amount of excess hydrogen peroxide to be neutralized. Selection of an appropriate quantity of reducing agent is a matter of routine for those of ordinary skill in the art. Where a reductase is present, the quantity of reducing agent can be lowered by as much as one-half. If present, the reductase will comprise between 0.2% and 2% of the total weight of the composition.

The most preferred form of the composition is a unit dosage tablet. The tablet can be jacketed or unjacketed. If jacketed, the sequestering agent can be included with the neutralizing system in the jacket or in the tablet core. If present in the jacket, the sequestering agent would dissolve into the hydrogen peroxide disinfecting solution before its neutralization, thus slowing the neutralization reaction and limiting the foaming which may result from the reaction.

If desired, other antifoaming agents can be included in the tablet (preferably in the jacket, if present). These agents are well-known in the art and include commercially available dimethylpolysiloxanes, paraffins or hydrophobically treated silicas. Tabletting agents, buffers and biocides, as well as preservatives, fillers and other inert delivery agents known to those skilled in the art can also be included in the composition as long as they do not interfere with the activity of the neutralizing system or sequestering agent.

The composition of the invention can also be in a sterile, isotonic saline solution, capsule or powder form. The composition can also be used in a delayed-release form; suitable means for delaying the release of the composition into the hydrogen peroxide solution for use in the composition will be apparent to those of skill in the art.

In a method of the invention, the composition described above is added (separately or by delayed-release) to a solution of hydrogen peroxide which has been used in a conventional disinfection regime for contact lenses (such as is practiced using the OXYSEPT and ULTRACARE disinfection systems sold by Allergan of Irvine, California). The lenses may also be cleaned with other conventional cleaners (such as a protease composition) before or after use of the inventive composition.

It can be expected that at least 30° C. and up to about 40° C. will be generated from the exothermic reaction between the reductase enzyme and hydrogen peroxide. Where a reducing agent is present, similar temperatures will be achieved. Those skilled in the art will be able readily to determine how much reductase should be present in the composition to moderate the exothermicity of the neutralization reaction to an extent sufficient to avoid lens damage.

The amount of inorganic deposits on a contact lens can be determined in a number of ways in order to determine the extent to which the accumulation of inorganic deposits is prevented. Examination of the lens by a trained optometrist while the lens is in the eye of the user, such as by a slit-lamp examination, can provide an estimate of the amount of inorganic deposits present on the lens. Comparison of the observed amount before and after treatment according to the present invention provides an estimate of the extent to which the accumulation of inorganic deposits on the lens is prevented.

Alternatively, the number of inorganic deposits can be observed under magnification ($10x$ to $100x$) in vitro and counted. Comparison of the counts before and after treatment will then provide an estimate of the extent of prevention of accumulation.

Other methods of determining the amount of inorganic deposits on a contact lens known to those skilled in the art can also be used to estimate the extent of prevention of accumulation resulting from treatment according to a method of the present invention. If desired, a quantitative level of reduction, such as 40% to 75%, can be established, and treatment of the lens according to a method of the present invention can be carried out until the selected level of reduction is achieved.

The length of time that the lenses remain in the solution of hydrogen peroxide and the inventive composition will vary according to the regime used, whether a reduction neutralizing system is used and if the composition is in a delayed-release form. The degree of cleaning or prevention of deposit accumulation is determined by the temperature reached during the reaction and the length of exposure of the contact lenses to the preparation.

Typically, the treatment time will vary from about 10 minutes to 12 hours (i.e, overnight). Twenty minutes is the recommended time for exposure to the reductase neutralizing system containing compositions and at least 2 hours is the preferred exposure time for all delayed-release compositions. Those skilled in the art will know how to modify the recommended treatment times as appropriate for the particular composition being used. Also, the contact lens wearer may increase the treatment time or perform more frequent treatments to ensure that the lenses are exposed to the sequestering agent and thus improve the preventive care of the lenses.

What is claimed is:

1. A composition for use with a hydrogen peroxide disinfecting system in a method for preventing the accumulation of inorganic deposits on a contact lens comprising (A) a sequestering agent selected from the group consisting of sodium borogluconate and sodium gluconate, and
(B) a neutralizing system capable of reducing the hydrogen peroxide in an exothermic reaction producing heat at a temperature of at least 30° C. without external application of heat, thereby activating said sequestering agent, said composition being free of hydrogen peroxide.

2. A composition for use with a hydrogen peroxide disinfecting system in a method for preventing the accumulation of inorganic deposits on a contact lens, said composition being in the form of a tablet having a jacket and a core, said composition comprising (A) a sequestering agent in said jacket or in said core, and
(B) a neutralizing system capable of reducing the hydrogen peroxide in an exothermic reaction producing heat at a temperature of at least 30° C. without external application of heat, thereby activating said sequestering agent, said composition being free of hydrogen peroxide.

3. A composition according to claim 2 wherein the neutralizing system consists essentially of a reductase.

4. A composition according to claim 2 wherein the neutralizing system consists essentially of a nonenzymatic reducing agent.

5. A composition according to claim 2 wherein the neutralizing system comprises a reductase and a reducing agent selected from the group consisting of ascorbic acid, sodium ascotbate, pyruvate and thiosulfate.

6. A composition according to claim 2 wherein the sequestering agent is selected from the group consisting of gluconic acid, polymetaphosphates, and their salts.

7. A composition according to claim 6 wherein the sequestering agent comprises sodium hexametaphosphate.

* * * * *